United States Patent [19]

Ooms et al.

[11] Patent Number: 5,527,942
[45] Date of Patent: Jun. 18, 1996

[54] PROCESS FOR THE PRODUCTION OF ARYL CARBONATES

[75] Inventors: Pieter Ooms, Krefeld; Norbert Schön, Darmstadt; Hans-Josef Buysch, Krefeld, all of Germany

[73] Assignee: Bayer AG, Leverkusen, Germany

[21] Appl. No.: 306,630

[22] Filed: Sep. 15, 1994

[30] Foreign Application Priority Data

Sep. 28, 1993 [DE] Germany .................. 43 32 979.9

[51] Int. Cl.$^6$ .................................................. C07C 68/02
[52] U.S. Cl. ............................................... 558/274
[58] Field of Search ........................................ 558/274

[56] References Cited

U.S. PATENT DOCUMENTS 5,239,105  8/1995  Pews et al. ........................ 558/274

FOREIGN PATENT DOCUMENTS

WO9106526  5/1991  WIPO.

Primary Examiner—Johann Richter
Assistant Examiner—Michael G. Ambrose
Attorney, Agent, or Firm—Connolly & Hutz

[57] ABSTRACT

Carbonates with aromatic ester groups can be produced by reaction of aromatic monohydroxy compounds with phosgene or with chloroformic acid esters of aromatic monohydroxy compounds, working at a temperature in the range of 50° to 350° C. in presence of oxides of the metals of Group IV B of the Mendeléeff periodic table as heterogeneous catalysts.

2 Claims, No Drawings

PROCESS FOR THE PRODUCTION OF ARYL CARBONATES

The invention relates to a process for the production of carbonates with aromatic ester groups by reaction of aromatic monohydroxy compounds with phosgene or chloroformic acid esters of aromatic monohydroxy compounds with elimination of hydrogen chloride in presence of oxides of metals of Group IV B of the Mendeléeff periodic table as heterogeneous catalysts.

Carbonates with aromatic ester groups are suitable for the production of polycarbonates by the melt esterification process and for the production of phenylurethanes or are intermediates for active substances from the pharmaceutical and plant-protection sector.

It is known that aryl carbonates can be obtained by phase interface phosgenation (Schotten-Baumann reaction) of aromatic hydroxy compounds. In this process the use of solvents and caustic soda solution is a disadvantage, since a partial saponification of phosgene or chloroformic acid ester can occur as a result of the aqueous alkali solution. In any case large amounts of common salt are obtained as by-product. Care must be taken, furthermore, to recover the solvent.

A condensation without co-utilization of solvents in presence of tetramethylammonium halides as catalysts has therefore been proposed (U.S. Pat. No. 2,837,555). Here, however, the amounts of catalyst required are relatively large. The process must usually be carried out with 5 to 7 wt % of catalyst, relative to the amount of phenol used, in order to obtain economic reaction rates, and the reaction temperatures of 180° C. to 215° C. are accompanied by the risk of a decomposition of the thermolabile tetramethylammonium halides. The catalyst must furthermore be subsequently removed by washing with water, whereby its recovery is considerably complicated. Moreover far more than the stoichiometrically required amount of phosgene is consumed.

According to another process (U.S. Pat. No. 3,234,263), diaryl carbonates are obtained by heating phenyl chloroformic acid esters in the presence of large amounts of alkali(alkaline earth) metal compounds with tertiary nitrogen bases as catalysts. However, this process has the disadvantage that high temperatures are used and the catalysts such as alkali(alkaline earth) compounds must partly dissolve in order to achieve only approximately economically justifiable reaction times. In this process, half of the phosgene originally used is lost in the form of $CO_2$. In addition, the chloroformic acid ester must be synthesized in a separate process stage.

According to CA-A-2 058 359 (U.S. Pat. No. 5,167,946) diaryl carbonates are obtained by phosgenation of aromatic hydroxy compounds in presence of aluminium compounds that are at least partly soluble under reaction conditions, or are transformed to soluble aluminium halides and apparently in this way act as homogeneous catalysts (cf. U.S. Pat. No. 2,362,865, column 1, lines 45 to 53). Aluminium trichloride is also particularly preferred for that reason (solubility). Although very good yields are obtained, it is difficult to separate the catalysts from the products. Even a certain volatility of these compounds during distillations must be taken into account, as well as thermal decompositions owing to these aluminium compounds, which lead to impurities, decreases of quality and yield losses. Similar remarks apply to the process of U.S. Pat. No. 2,362,865, which also quotes the use of titanium, iron, zinc and tin as metals or in the form of their soluble salts, particularly the chlorides and phenolates.

It therefore appears reasonable to use heterogeneous insoluble catalysts, that considerably simplify the workup of the reaction mixture. Proposals have also been made to that end. Thus, according to the teaching of EP-A-516 355, aluminium trifluoride, which is optionally applied to supports such as aluminosilicates, has been particularly recommended. However, the synthesis of aluminium fluoride is very complicated and expensive owing to the handling of fluorine or hydrofluoric acid. Furthermore, metal salts on porous supports are described in WO 91/06526 as catalysts for the reactions according to the invention. As is evident from the experimental examples, a fully continuous phosgenation of phenol on such catalysts is possible only in the gas phase, which, however, is accompanied by relatively high reaction temperatures and the risk of the decomposition of the sensitive chloroformate ester. Obviously a phosgenation of phenol cannot be carried out in the liquid phase with these catalysts, since the hot liquid phenol leaches out the active catalyst ingredients.

The object of the invention therefore consisted in the development of simple, accessible, active, heterogeneous catalysts.

It has now been found that oxides of the metals of Group IV B of the Mendeléeff periodic table are excellent catalysts for the reaction of phosgene or chloroformic acid esters with aromatic hydroxy compounds. This is particularly surprising and unexpected since such compounds are known as inert according to the previous teaching of WO 91/06526. There is no mention of a catalytic activity for the purposes of the present invention. On the contrary, titanium oxide and zirconium oxide are mentioned preferably as resistant and inert support materials.

The present invention accordingly provides a process for the production of aryl carbonates by reaction of aromatic monohydroxy compounds with phosgene or chloroformic acid esters of aromatic monohydroxy compounds, which is characterized in that it is carried out at temperatures in the range of 50° to 350° C., optionally at a pressure of 0.2 to 20 bar in presence of oxides of the metals of Group IV B of the Mendeléeff periodic table as heterogeneous catalysts.

The process according to the invention has the great advantage that the catalyst can very easily be separated off and no impurities remain in the crude reaction product. As a result, the workup is considerably simplified.

Aromatic monohydroxy compounds for the process according to the invention are those of the formula $$Ar^1\text{-OH} \qquad (I),$$

wherein
  $Ar^1$ signifies phenyl, naphthyl, anthryl, phenanthryl, indanyl, tetrahydronaphthyl or the group of a 5- or 6-membered aromatic heterocyclic compound with 1 or 2 heteroatoms from the group of N, O and S, wherein these isocyclic and heterocyclic groups can be substituted by 1 or 2 substituents such as straight-chain or branched $C_1$–$C_4$ alkyl, straight-chain or branched $C_1$–$C_4$ alkoxy, that can be substituted with phenyl, cyano and halogen (e.g. F, Cl, Br) and wherein furthermore the heterocyclic groups can be linked with another fused benzene ring.

Examples of aromatic monohydroxy compounds of formula (I) are: phenol, o-, m- and p-cresol, o-, m- and p-isopropylphenol, the corresponding halogeno- or alkoxyphenols, such as p-chlorophenol or p-methoxyphenol and furthermore monohydroxy compounds of naphthalene, anthracene and phenanthrene, and moreover 4-hydroxypyridine and hydroxyquinolines. Optionally substituted phenols are preferably used, and especially phenol itself.

The process according to the invention can be carried out both with phosgene and with chloroformic acid esters of aromatic monohydroxy compounds. In the case where the process is carried out with phosgene, the chloroformic acid ester is formed first and is converted by additional aromatic hydroxy compound present in the reaction mixture to the diaryl carbonate.

If one starts from chloroformic acid esters and an aromatic monohydroxy compound, symmetrical or unsymmetrical carbonates can be obtained.

Suitable aromatic chloroformic acid esters for the process according to the invention are accordingly those of formula (II)

$$Ar^1\text{-OCOCl} \qquad (II)$$

wherein $Ar^1$ has the significance indicated in the case of formula (I).

Suitable metal oxides for the purposes of the invention are oxides of titanium, zirconium and hafnium. They can exist in crystalline form in various modifications. They can be wholly or partially amorphous.

Such metal oxides and their origin as well as production processes for such compounds are described for example in Kirk-Othmer, Encyclopedia of Chemical Technology, 3rd Edition, volume 17, p. 801 ff, volume 23, p. 137 ff, volume 24, p. 882 ff, volume 12, p. 77 ff, New York 1978 and Ullmann's Encyclopedia of Industrial Chemistry, 5th Edition, volume 17 ff, p. 430, Weinheim 1985.

Also to be considered are both metal oxides from natural sources, i.e. from various minerals such as e.g. ilmenite, and also those from other intermediates, as for example metal salts and metal alkoxides.

The metal oxides to be used in the process according to the invention are preferably oxides of tetravalent titanium, which can also contain oxides of titanium in lower oxidation states and oxides of tetravalent zirconium and hafnium, for example titanium dioxide, occurring as anatase, brookite or rutile, zirconium dioxide in the monoclinic (baddeleyite, zirconium earth), tetragonal, orthorhombic or cubic form and hafnium dioxide in various modifications.

The metal oxides for the purposes of the invention can be used dried, partially dried or as hydrates.

First to be formed by successive dehydration (calcination) of metal hydroxides and metal oxidehydroxides at temperatures of 80° to above 1200° C. are partially dehydrated metal oxides that still contain noticeable amounts of hydroxyl groups and with progressive dehydration change over into the anhydrous metal oxides. According to the nature of the starting hydroxide or oxidehydroxide, various aforementioned modifications of the metal oxide can be passed through.

The metal oxides can be used as such, preferably those which occur naturally, but they can also contain other elements such as alkali and alkaline earth metals, chromium, vanadium, manganese, zinc, iron or silicon in minor amount. The products preferably used have contents of such impurities of <2 wt %, particularly <1 wt %. Synthetic metal oxides are particularly pure. Preferred metal oxides have BET surfaces of 2 to 500 m²/g, particularly preferred those of 4 to 450 m²/g and especially preferred those of 5 to 400 m²/g. Acidic, neutral and basic oxides can be used.

The catalysts can be used e.g. as powder or moulded bodies and separated off after the reaction e.g. by filtration, sedimentation or centrifuging. In the case of a fixed bed arrangement, the metal oxides are preferably used as moulded bodies, e.g. as spheres, cylinders, rods, hollow cylinders, rings etc.

In operation with a suspended catalyst, the metal oxide catalysts are used in agitated vessels or bubble columns in amounts of 0.5 to 100 wt %, preferably of 5 to 100 wt % and particularly of 5 to 50 wt %, relative to the amount of monohydroxy compound used.

In the case of a continuous mode of operation in counter- or cocurrent or in the trickle phase on the fixed-bed catalyst, catalyst loadings of 0.1 to 20 g aromatic hydroxy compound per g catalyst per hour, preferably 0.2 to 10 $g \cdot g^{-1} \cdot h^{-1}$ and particularly 0.2 to 5 $g \cdot g^{-1} \cdot h^{-1}$ are used.

The metal oxides used in discontinuous experiments can be used repeatedly with the same feed materials without cleaning. In case of a change of feed materials, the metal oxides are expediently cleaned by extraction with inert solvents, such as are mentioned for example below as reaction media, or with alcohols, such as methanol, ethanol, isopropanol or butanol, with esters or amides of acetic acid or by treatment with superheated steam or air.

During continuous operation, the metal oxides used can remain in the reactor for a long time. A regeneration can be carried out by passing superheated steam over, optionally with addition of minor amounts of air (about 0.1 to 20 wt % relative to the amount of steam used) at 150° to 800° C. or by passing over diluent gases, such as nitrogen or carbon dioxide, containing 0.01 to 20 wt % oxygen or by carbon dioxide alone at 200° to 800° C. The preferred regeneration temperature is 150° to 700° C., particularly 200° to 600° C.

The process according to the invention is carried out at a temperature in the range of 50° to 350° C., preferably 100° to 300° C. particularly 100° to 250° C. During the carrying out of the process according to the invention, the temperature can be changed, preferably raised, in the range mentioned.

The process is carried out at a pressure of 0.2 to 20 bar, preferably 1 to 5 bar.

The process according to the invention can be carried out with the participation of solvents, such as aliphatic and aromatic hydrocarbons, such as pentane, hexane, octane, benzene, xylene isomers, diethylbenzene, alkylnaphthalenes, biphenyl; and halogenated hydrocarbons such as dichloromethane, trichloroethylene etc.

The process is preferably carried out in the melt, for example by introducing phosgene or a chloroformic acid ester of formula (II) into a suspension of a metal oxide in a melt of the aromatic monohydroxy compound of formula (I) and, after completion of the reaction, separating off the catalyst, e.g. by filtration or centrifuging.

Another preferred embodiment of the synthesis is the gassing of a melt of the aromatic monohydroxy compound of formula (I), with a metal oxide catalyst suspended therein, with phosgene or phosgene-hydrogen chloride mixtures or with chloroformic acid esters of formula (II) in a continuous bubble column or a bubble-column cascade.

Another preferred embodiment is the cocurrent process, wherein aromatic hydroxy compounds of formula (I) and phosgene or chloroformic acid esters of formula (II) are introduced in cocurrent, for example from above onto a catalyst bed arranged in a tube, and hydrogen chloride and phosgenation products are withdrawn below at the foot of the tube.

Another preferred embodiment with particularly favourable results is the carrying out of the reaction according to the invention in the trickle phase, wherein the aromatic monohydroxy compound of formula (I) is introduced from above as a melt or in the form of a solution onto a bed of metal oxide and a stream of phosgene or chloroformic acid ester is supplied to this liquid stream in the contrary direction from below. This embodiment is expediently carried out in a vertical tubular reactor, which can also contain intermediate plates for the improved distribution of gas stream and liquid stream.

The molar ratio of the reactants, aromatic monohydroxy compounds of formula (I) to phosgene, is 0.5 to 8:1, preferably 1.5 to 3:1. The equivalent molar ratio is in this case 2:1.

Correspondingly, the aromatic monohydroxy compound is reacted with a chloroformic acid ester in the molar ratio of 0.25 to 4:1, preferably 0.8 to 1.5:1. In this case the molar ratio is 1:1.

The crude aromatic carbonate obtained by heterogeneous catalysis is frequently very pure already and, after degassing of residual hydrogen chloride or other volatile substances, can already be used in this form for many purposes. For more demanding applications, the carbonate can be further purified, optionally e.g. by distillation or crystallization.

EXAMPLES

Example 1

In a plane-joint jar with flow spoilers, a gas-dispersion stirrer and reflux condenser, 0.75 mol/h phosgene was continuously bubbled into 141 g (1.50 moles) of phenol at 140° C. in the presence of 14.1 g (10 wt % relative to phenol) of a powdered titanium dioxide from the Riedel de Haen company. After about 2 h reaction time, the phenol conversion was 12.5%, whereby 0.7 g phenyl chloroformate and 19.5 g diphenyl carbonate were formed. The selectivity to carbonate esters was >99%.

Example 2

Example 1 was repeated at 140° C. with 14.1 g of a granular (4 to 5 mm diameter) titanium dioxide, Calsicat 20503, from the Calsicat company. After 2 h reaction time, the phenol conversion was 7.2%, whereby 0.8 g phenyl chloroformate and 11.0 g diphenyl carbonate were formed. The selectivity to carbonate esters was >99%.

Example 3

Example 1 was repeated at 140° C. with 14.1 g of a powdered zirconium dioxide from the Aldrich company. After 2 h reaction time, the phenol conversion was 6.3%, whereby 3.2 g phenyl chloroformate and 7.8 g diphenyl carbonate were formed. The selectivity to carbonate esters was greater than 99%.

Example 4

Example 1 was repeated at 140° C. with 14.1 g of a powdered hafnium dioxide from the Aldrich company. After 2 h reaction time, the phenol conversion was 3.7%, whereby 3.5 g phenyl chloroformate and 3.3 g diphenyl carbonate were formed. The selectivity to carbonate esters was ca. 97%.

Example 5 (For Comparison)

Example 1 was repeated at 140° C. without addition of metal oxide. After 2 h reaction time, the phenol conversion was less than 0.2%.

Example 6

In a three-necked flask with thermometer and reflux condenser, a mixture of 9.4 g (0.10 mol) phenol and 15.7 g (0.10 mole) phenyl chloroformate is heated in presence of 0.94 g (10 wt % relative to phenol) of a powdered titanium dioxide from the Fluka company at 100° C. After 5 h reaction time a phenol conversion of 2.1% to diphenyl carbonate is found. The carbonate selectivity was >99%.

Example 7

Example 6 was repeated with the same catalyst at 120° C. After 3 h reaction time the phenol conversion to diphenyl carbonate was 22.3%. The carbonate selectivity was >99%.

Example 8

Example 6 was repeated with the same catalyst at 140° C. After 5 h reaction time the phenol conversion to diphenyl carbonate was 83.8%. The carbonate selectivity was >99%.

Example 9

Example 6 was repeated with the same catalyst at 160° C. After 1 h reaction time the phenol conversion to diphenyl carbonate was 99%. The carbonate selectivity was >99%.

Example 10

Example 6 was repeated with 0.94 g of a powdered titanium dioxide (rutile) from the Bayer company at 160° C. After 1 h reaction time the phenol conversion to diphenyl carbonate was 100%. The carbonate selectivity was >99%.

Example 11

Example 6 was repeated with 0.94 g of a granular titanium dioxide (4–5 mm diameter), Calsicat 20503, from the Calsicact company at 160° C. After 1 h reaction time the phenol conversion to diphenyl carbonate was 63.2%. The carbonate selectivity was >99%.

Example 12

Example 6 was repeated with 0.94 g of a powdered titanium dioxide (anatase) from the Bayer company at 160° C. After 1 h reaction time the phenol conversion to diphenyl carbonate was 77.3%. The carbonate selectivity was >99%.

Example 13

Example 6 was repeated with 0.94 g of a powdered zirconium dioxide from the Aldrich company at 160° C. After 3 h reaction time the phenol conversion to diphenyl carbonate was 86.5%. The carbonate selectivity was >99%.

Example 14

Example 6 was repeated with 0.94 g of a powdered hafnium dioxide from the Aldrich company at 160° C. After 5 h reaction time the phenol conversion to diphenyl carbonate was 63.1%. The carbonate selectivity was >99%.

We claim:
1. A process for the production of aryl carbonates which comprises reacting aromatic monohydroxy compounds with phosgene or chloroformic acid esters of aromatic monohy- droxy compounds at temperatures in the range of 50° to 350° C., at a pressure of 0.2 to 20 bar, and in the presence of one or more oxides of the metals of Group IV B of the Mendeléeff periodic table as heterogeneous catalysts.

2. A process according to claim 1, wherein said oxides have surface areas determined by the BET method of 2 to 500 m$^2$/g and are used in amounts of 0.5 to 100 w %, relative to the amount of monohydroxy compound in the case of not fully continuous operation or with loadings of 0.1 to 20 g monohydroxy compound per g catalyst per hour in the case of fully continuous operation.

* * * * *